(12) United States Patent
Marcucci et al.

(10) Patent No.: US 6,172,202 B1
(45) Date of Patent: *Jan. 9, 2001

(54) SYNTHESIS OF POLYMER BIO-ACTIVE CONJUGATES

(75) Inventors: Fabrizio Marcucci, Legnano; Ruth Gregory, Milan, both of (IT)

(73) Assignee: Pharmacia S.p.A., Milan (IT)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/889,049

(22) Filed: Jul. 7, 1997

Related U.S. Application Data

(63) Continuation of application No. 08/424,548, filed as application No. PCT/EP93/03429 on Dec. 6, 1993, now abandoned.

(30) Foreign Application Priority Data

Dec. 4, 1992 (GB) .................................................. 9225448

(51) Int. Cl.$^7$ .......................... C07G 17/00; A61K 39/00; A61K 39/395
(52) U.S. Cl. ....................... 530/406; 424/178.1; 435/180; 530/402
(58) Field of Search ................................ 435/391.1, 410, 435/411, 179.1, 972; 424/181.1, 133.1, 178.1; 530/406, 402

(56) References Cited

U.S. PATENT DOCUMENTS

| | | | |
|---|---|---|---|
| 4,699,784 | * | 10/1987 | Shih et al. .......................... 424/181.1 |
| 4,732,863 | * | 3/1988 | Tomasi et al. ..................... 530/391.1 |
| 4,863,729 | * | 9/1989 | Zuckerkandl ...................... 424/178.1 |
| 5,047,227 | * | 9/1991 | Rodwell et al. ................... 424/181.1 |
| 5,314,830 | * | 5/1994 | Anderson et al. ................. 530/391.1 |
| 5,556,623 | * | 9/1996 | Barton et al. ..................... 424/181.1 |
| 5,705,158 | * | 1/1998 | Hansen et al. .................... 424/181.1 |

FOREIGN PATENT DOCUMENTS 0 586 500 A1    3/1993 (EP) .

OTHER PUBLICATIONS

Chemical Abstracts, vol. 114, No. 3, Jan. 21, 1991, JP,A,2 21 162.
Chemical Abstracts, vol. 111, No. 5, Jul. 31, 1989, Nonpecific Reaction in the Sandwich Immunoassay for Human Necrosis Factor–Alpha.
Molecular Immunology, vol. 30, No. 12, Aug. 1993, pp. 1123–1131, A Corti Evidences that Syngeneic Alpha–Type Anti–Idiotypic Antibodies May Non–Completitively Inhibit Idiotype/oligomeric Antiben Interactions by Affecting Idiotype Adivity.
Hybridoma, vol. 12, No. 1, Feb. 1993, pp. 1–13, Mode of Interaction Between Tumor Necrosis Factor and a mOAB Expessing A Recurrent Idiotype.
International Publication No. WO 93/15189 published Aug. 5, 1993.
Abstract (Dialog) of Bitoh et al Hum Antibodies Hybridomas (U.S.) Jul. 1993 4(3) pp. 144–151.*

* cited by examiner

Primary Examiner—Peter F. Kulkosky
(74) Attorney, Agent, or Firm—Arent Fox Kintner Plotkin Kahn

(57) ABSTRACT

A process for the preparation of a conjugate between a poly (ethylene glycol) and a protein or glycoprotein, the process comprising specifically binding the domain to a specific binder, to shield the domain from the poly (ethylene glycol) in the following conjugating step, thereafter conjugating the poly (ethylene glycol) to the protein or glycoprotein, wherein conjugation of the poly (ethylene glycol) to the domain is avoided and thereafter releasing the specific binder from the domain without releasing the poly (ethylene glycol) from the protein or glycoprotein, wherein the protein or glycoprotein is other than a proteolytic enzyme selected from the group consisting of trypsin, urokinase, tissue plasminogen activator, plasmin, chymotrypsin, elastase and kallikrein.

8 Claims, 3 Drawing Sheets

SYNTHESIS OF POLYMER BIO-ACTIVE CONJUGATES

Figure 1:
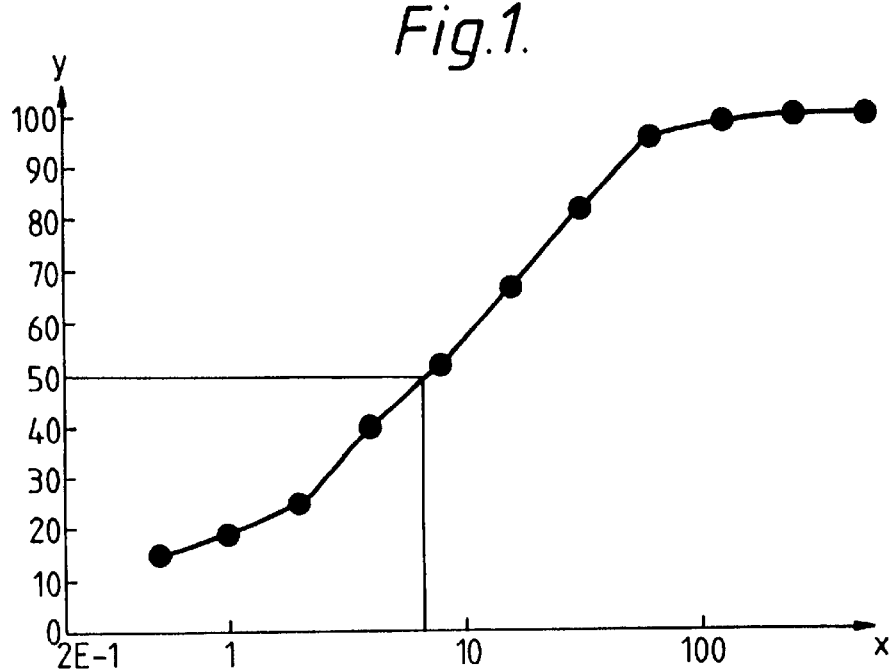

This application is a continuation of application Ser. No, 08/424,548, filed Jun. 2, 1995, now abandoned, which is a 371 of International Application Ser. No. PCT/EP93/03429, filed Dec. 6, 1993, the entire disclosures of which are hereby incorporated by reference.

The present invention relates to a process for the preparation of a conjugate between a polymer and a bioactive substance.

In the last decade a steadily increasing number of proteins have entered routine clinical use as therapeutic or diagnostic agents (see, for example, Waldmann, T. A., *Science,* 252 : 1657–1662, 1991 and Jaffe, H. S. and Sherwin, S. A., *Drugs of Today,* 25 : 311–320, 1989 and Foon, K. A., *Cancer Research,* 49 : 1621–1639, 1989). The efficacy of many of these agents, however, is limited for two main reasons.

First, the in vivo half-life is often very short (see, for example, Mühlradt, P. F. and Opitz, H. G., *European Journal of Immunology,* 12: 983–985, 1982 and Jacobs, C. A., Lyncl, D. H., Roux, E. R., Miller, R., Davis, B., Widmer, M. B., Wignall, J., VandenBos, T., Park, L. S. and Beeckmann, M. P., *Blood,* 77 : 2396–2403, 1991 and Blick, M., Sherwin, S.A., Rosenblum, M. and Gutterman, J., *Cancer Research,* 47 : 2986–2989, 1987).

Second, in case of heterologous proteins, another problem adds to the first. This is due to the proteins being recognized as foreign substances (antigens) by the immune system of the species treated, thereby leading to an immune response that abolishes, upon a second administration, the pharmacological activity of the heterologous protein (see, for example, Shawler, D. L., Bartholomew, R. M., Smith, L. M. and Dillman, R. O., *Journal of Immunology,* 125: 1530–1535, 1985 and Schroff, R. W., Foon, K. A., Beatty, S. M., Oldham, R. K. and Morgan, A. C., *Cancer Research,* 54 : 879–885, 1985 and Traub, U. C., De Jager, R. L., Primus, F. J., Losman, M. and Goldenberg, D. M., *Cancer Research,* 48 : 4002–4006, 1988).

For these reasons methods have been sought to overcome either one or both of the above mentioned problems, i.e. to prolong the in vivo half-life of proteins and to reduce their antigenicity in case of proteins heterologous with respect to the species to be treated. One particular approach that has been taken is to conjugate proteins to soluble synthetic polymers, in particular poly(ethylene glycol), poly(vinyl pyrrolidone), poly(vinyl alcohol), poly(amino acids), divinylether maleic anhydride, ethylene-maleic anhydride, N-(2-hydroxypropyl)methacrylamide and dextran (see, for example, Abuchowski, A., Van Es, T., Palczuk, N. C. and Davis, F. F. *Journal of Biological Chemistry* 11, 3578–3581, 1977; Yasuda, Y., Fujita, T., Takakura, Y., Hashida, M., and Sezaki, H. *Chemistry and Pharmaceutical Bulletin* 38, 2053–2056, 1990; Fagnani, R., Hagan, M. S. and Bartholomew, *Cancer Research* 50, 3638–3645 (1990); Suck, J. M. and Wild, B. S. U.S. Pat. No. 3,679,653, 1972; Flanagan, P. A., Duncan, R., Rihova, B., Subr, V. and Kopecek, J., *Journal of Bioactive and Compatible Polymers* 5, 151–166, 1990.

More than 40 proteins have now been modified, mainly using polyethylene glycol, but it has been shown that a variety of other polymers can be substituted to provide reduced immunogenicity and protein stabilisation. In particular, the approach has been used to modify enzymes including arginase, asparaginase, adenosine deaminase galactosidase, lipase, pro-urokinase, streptokinase, superoxide dismutase, trypsin and uricase (see, for example, Nucci, M. L., Shorr, R. and Abuchowski, A. *Advanced Drug Delivery Reviews* 6, 133–151, 1991; Veronese, F. M., Caliceti, P., Pastorino A., Schisvon, O., and Sartore. *Journal of Controlled Release* 10, 145–154, 1989); cytokines and growth factors such as interleukin 2 and human granulocyte colony-stimulating factor (see, for example, Katre, N. V. *Journal of Biological Chemistry* 144, 209–213, 1990; Tanaka, H., Satake-Ishikawa, R., Ishikawa, M., Natsuki, S. and Asano, K. *Cancer Research* 51, 3710–3714, 1991) and antibodies (see, for example, Kitamura, K., Takahashi, T., Yamaguchi, T., Noguchi, A., Takashina, K., Tsurumi, H., Inagake, M., Toyokuni, T. and Hakomori, S. *Cancer Research* 51, 4310–4315, 1991).

A number of methods have been described for linkage of polymers to bio-active protein molecules (see, for example, U.S. Pat. No. 4,179,337, U.S. Pat. No 4,732,863, Jackson C.-J., Charlton, J. L., Kuzminski, K., Lang, G. M. and Sehon A. H. *Analytical Biochemistry* 165, 114–127, 1987; Veronese, F., M., Largajolli, R., Boccu, E., Benassi, C. A. and Schiavon, O. *Applied Biochemistry and Biotechnology* 11, 141–152, 1985 ; WO93/15189). However, the methods currently available for conjugation have two major drawbacks. Usually, other than the Veronese approach in WO93/15189, first, the derivatisation procedures reported are inherently random thereby leading to the introduction of polymeric moieties into domains of the molecule that mediate the therapeutically or diagnostically desirable activity (ies). Consequently, the molecule may acquire a prolonged half-life in vivo and, in case of heterologous proteins, reduced immunogenicity, but at the expense of a significant or complete loss of the desired biological activity(ies) (see, for example, Kitamura, K., Takahashi,T.,Yamaguchi,T., Noguchi,A.,Noguchi, A., Takashima, K.-i., Tsurumi, H., Inagake, M., Toyokuni, T. and Hakanori, S.-i., *Cancer Research,* 51: 4310–4315, 1991 and Maiti, P. K., Lang, G. M. and Sehon, A. H., *International Journal of Cancer, Supplement* 3: 17–22, 1988).

Loss of biological activity following polymer conjugation has been observed in the case of both antibodies and enzymes, particularly when access of the modified protein to a macromolecular substrate or receptor is essential to produce biological activity. However, it has been found that inactivation of enzymatic activity is not necessarily a result of polymer conjugation if the domain(s) mediating activity either do not contain functional groups suitable for polymer derivatisation, and/or the binding of polymer molecule(s) does not sterically hinder access of low molecular weight enzyme substrates.

In fact, enzymes like adenosine deaminase and L-asparaginase have been successfully conjugated with polyethylene glycol (see, for example, Hershfield, M. S., Buckley, R. H., Greenberg, M. L., Melton, A. L., Schiff, R., Hatem, C., Kurtzberg, J., Markert, M. L., Kobayashi, R. H., Kobayashi, A. L. and Abuchowski, A., *The New England Journal of Medicine,* 316 : 589–596, 1987 and Teske, E., Rutteman, G. R., van Heerde, P. and Misdorp, W., *European Journal of Cancer,* 26: 891–895, 1990). In one case (adznosine deaminase) the product thereby obtained has received approval for clinical use in humans. These examples, however, are the exception rather than the rule.

A second problem associated with synthesis of polymer-protein conjugates has been heterogeneity of the product formed. Polymers are by nature heterogeneous, displaying within any sample a range of molecular weights, ie. they are polydisperse, and in addition any preparation also displays a heterogeneity in the number of functional groups available for attachment to the protein to be modified. Thus, during the conjugation reaction there is opportunity to form a multitude of products. This problem has been previously been exacerbated by the need to control carefully the degree of protein modification to a minimum to ensure retention of substantial biological activity of the protein, whilst concurrently introducing a sufficient number of polymer molecules into the conjugate to facilitate the needed reduction in immunogenicity, and protein stabilisation.

According to the present invention, there is provided a process for the preparation of a conjugate between a polymer and a first substance having a biological activity mediated by a domain thereof, which process comprises:
(a) contacting the first substance with a second substance which specifically binds to the said domain of the first substance;
(b) conjugating a polymer to the first substance having the second substance bound thereto; and
(c) freeing the second substance from the first substance having the polymer conjugated thereto, and wherein, when the first substance is a proteolytic enzyme chosen from trypsin, urokinase, tissue plasminogen activator, plasmin, chymotrypsin, elastase and kallikrein then the polymer is other than polyethylen glycol.

A significant improvement can thus be achieved. The procedure of the invention preserves the advantages deriving from the conjugation of polymers to therapeutically or diagnostically useful molecules, i.e. prolonged half-life in vivo and reduced immunogenicity in case of heterologous proteins. Further, a desired biological activity is not lost and a homogeneous product can be attained.

The invention relies upon the use of a second substance that specifically recognizes a domain that mediates the desired biological activity of a first substance which is to be derivatized. The second substance can be viewed as a specific binder substance. The first substance is allowed to interact with the specific binder before effecting polymer conjugation. This ensures that the domain of the first substance that mediates the desired biological activity of that substance is shielded and consequently unavailable for derivatization by the polymer. Following its elution from the specific binder, the conjugate between the polymer and the first substance can be recovered with fully preserved biological activity.

The first substance may be any molecule having a desired activity. The substance may be a physiologically active substance. The first substance is typically an organic macromolecular entity such as a protein or a glycoprotein. The second substance binds to a site on the first substance which mediates the activity of the first substance. The second substance therefore protects the active site of the first substance.

The invention may be applied broadly. The first substance may be an antibody or antibody fragment, cytokine, antigen, enzyme, ligand or receptor. The second substance may be, respectively, an antigen or antidiotypic antibody, receptor or anticytokine antibody, antibody, enzyme substrate, receptor or ligand. In each case the second substance specifically binds to the first substance to shield the domain of the first substance which is responsible for the activity of the first substance. Examples of pairs of first and second substances are as follows
1. When the first substance is a monoclonal antibody (mAb), including anti-idiotypic and anti-anti-idiotypic antibodies, or mAb fragment such as Fab'and F(ab)$_2$ fragments, the second substance may be the antigen to which the mAb or mAb fragment binds or an antibody including idiotypic, anti-idiotypic, anti-anti-idiotypic antibodies. The mAb or mAb fragment which constitutes the first substance may be specific for any appropriate antigen, for example human tumor necrosis factor α (hu TNFα). The mAb fragment may be non-human, for example a murine mAb or mAb fragment.
2. The first substance may be a protein and the second substance may be a ligand which specifically binds to an active site of the protein. The first substance may be a fibrinolytic enzyme such as pro-urokinase (pro-UK), urokinase (UK) or tissue plasminogen activator (tPa) or a fibrinolytic agent such as streptokinase or a non-protease enzyme, such as β-glucuronidase, purine nucleoside phosphorylase,bilirubin oxidase or superoxide dismutase. The second substance may be a mAb which is directed against the specific active site of the first substance. Alternatively the second substance may be the ligand with which the first substance normally interacts. For example:

First substance: streptokinase or hirudin, second substance plasminogen or thrombin respectively; and first substance: a growth factor such as FGF, EGF, PDGF, HGH or HGF, a growth factor receptor, a lymphokine or cytokine such as an inteteron, interleukin, stimulating factor, TNFα or TIFβ or a lymphokine or cytokine receptor; second substance the corresponding growth factor receptor, the corresponding growth factor, the corresponding lymphokine or cytokine receptor or the corresponding lymphokine or cytokine respectively.

The second substance may be a low molecular weight ligand. This applies generally to all therapeutic proteins having enzymic activity and to proteolytic enzymes. The therapeutic protein may be a fibrinolytic enzyme such as pro-UK, UK or tPA and the second substance may be benzamidine or a derivative thereof. A heparin-binding protein, for example a growth factor such as FGF or HGF, may be the first substance and heparin or a heparin-like molecule or a heparin derivative typically having a low molecular weight and a negative charge may constitute the second substance.

In other instances, the first substance may be a protein that interacts with a peptide ligand. This may be applied to any protein having a therapeutic application. The first substance may be a DNA binding protein and the second substance may be DNA or an oligonucleotide.

In some instances it may be desirable to preserve the biological activities mediated by two separate domains of the first substance. In such cases both biological activities can be preserved through the use of two specific binders each one recognizing one of the two biologically active domains. Thus, for example, monoclonal antibodies against tumor-associated antigens destroy the relevant target cells through binding on the one hand, to the antigen with their variable regions and, on the other hand, to killer cells (K cells) through their constant regions. The K cells become at this point the actual effector of the lytic process that leads to the destruction of the tumorigenic target cell. This process is called antibody-dependent cellular cytotoxicity.

In this case it would be desirable to preserve binding of the monoclonal antibody to both cell types (tumor cell and K cell). This can be achieved, according to the present invention, by performing the conjugation step after having shielded, on the one hand, the antigen-binding regions with the tumor-associated antigen and, on the other hand, the binding site for K cells with the K cell-receptor for the constant region of the monoclonal antibody.

The first substance's active domain is therefore protected by the second substance. The first substance can then be conjugated to a polymer. Generally the polymer is an inert, synthetic, polymeric carrier. The polymer is usually water-soluble.

The polymer may be poly(ethylene glycol) (PEG), poly(vinyl pyrrolidone), poly(vinyl alcohol), poly(amino acids), divinylether maleic anhydride, ethylene-maleic anhydride, N-(2-hydroxypropyl)-methacrylamide or dextran. The polymer may be derivatised or activated itself prior to use. PEGylation may be achieved using, for example, monomethoxypolyethylene glycol-succinimidyl succinate (mPEG). Coupling may be effected using techniques analogous to those already known in the art, for example according to U.S. Pat. No. 4,179,337, U.S. Pat. No. 4,732,863, WO 91/01758, WO 91/15242, U.S. Pat. No. 4,935,465 and U.S. Pat. No. 4,415,665.

Generally there is a molar excess of polymer with respect to the first substance. In accordance with the present invention the molar excess may be from 1 to 500 times, or higher, without there being any loss of function activity. Conjugation must be carried out under such conditions that the second substance does not disassociate from the first substance during the binding procedure. When the first substance is an antibody and the second substance is an anti-idiotypic antibody, therefore, the pH of the reaction medium is about 7, typically from about 6.3 to about 7.8, in particular about 7.2. Preferably conjugation is effected under conditions such that polymer is conjugated to the first substance at substitution levels for the reduction of immunogenic activity or elongation of the half-life of the biologically active substance. The person skilled in the art will appreciate that many other polymers can be used for this purpose. In a preferred embodiment, the specific binder that affords protection during the polymer conjugation step is first covalently linked to a solid phase such as column packing materials, for instance sephadex or agarose beads, or a surface, e.g. reaction vessel. This allows the polymer-derivatized first molecule to be separated from the specific binder by elution. The fluid phase containing the derivatized first substance is separated from the solid phase to which the specific binder remains covalently-linked. Such separation can be achieved by many other means. Thus, the specific binder may be derivatised itself with a third molecule (e.g. biotin) that can itself be recognized by a second specific binder (e.g. streptavidin). The second specific binder may be linked to a solid phase thereby allowing the separation of the polymer-derivatized first molecule from the first specific binder-third molecule complex through passage over a second specific binder-solid phase column which will retain, upon subsequent elution, the first specific binder-third molecule complex, but not the polymer-derivatized first molecule. The first substance to which the polymer is conjugated may be released from the second substance in any appropriate fashion. Deprotection may be achieved by providing conditions in which the second substance dissociates from the active domain of the first substance. A complex between an antibody to which a polymer is conjugated and an antiidiotypic antibody can be dissociated by adjusting the pH to an acid or alkaline pH.

The following Examples illustrate the invention.

In the accompanying drawings:

FIG. 1 shows the cytotoxic activity on LM cells of 1 ng/ml huTNFα in the presence of increasing concentrations of mAb78. The x-axis denotes the concentration of mAb78 in ng/ml. The y-axis denotes the percentage viability of LM cells in the presence of 1 ng/ml huTNFα and different concentrations of mAb78. The Figure indicates the concentration of mAb78 at which 1 ng/ml huTNFα exerts 50% cytotoxic activity (6.7 ng/ml).

Figure 2:
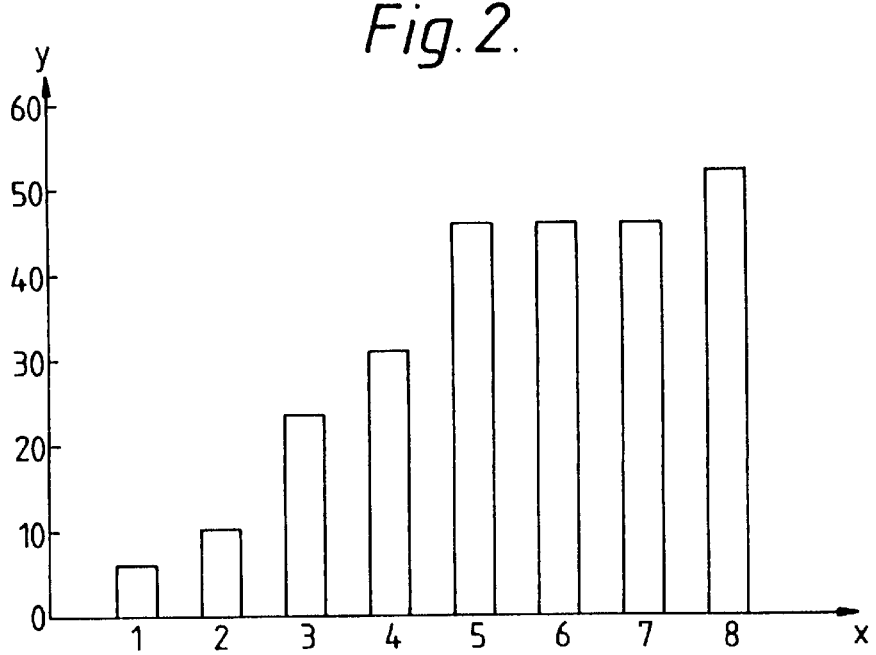

FIG. 2 shows the concentrations in ng/ml of mAb78 or unprotected mAb78-mPEG conjugates at which 1 ng/ml huTNFα exerts 50% cytotoxic activity on LM cells (y-axis). (1) mAb78; (2) unprotected mAb78 derivatized upon addition of a 3-fold molar excess of mPEG (mAb78+mPEG 3×); (3) mAb78+MPEG 15× (4) mAb78+mPEG 62.5×; (5) mAb78+mPEG 125×; (6) mAb78+mPEG 250×; (7) mAb78+mPEG 300×; (8) mAb78+MPEG 500×.

Figure 3:
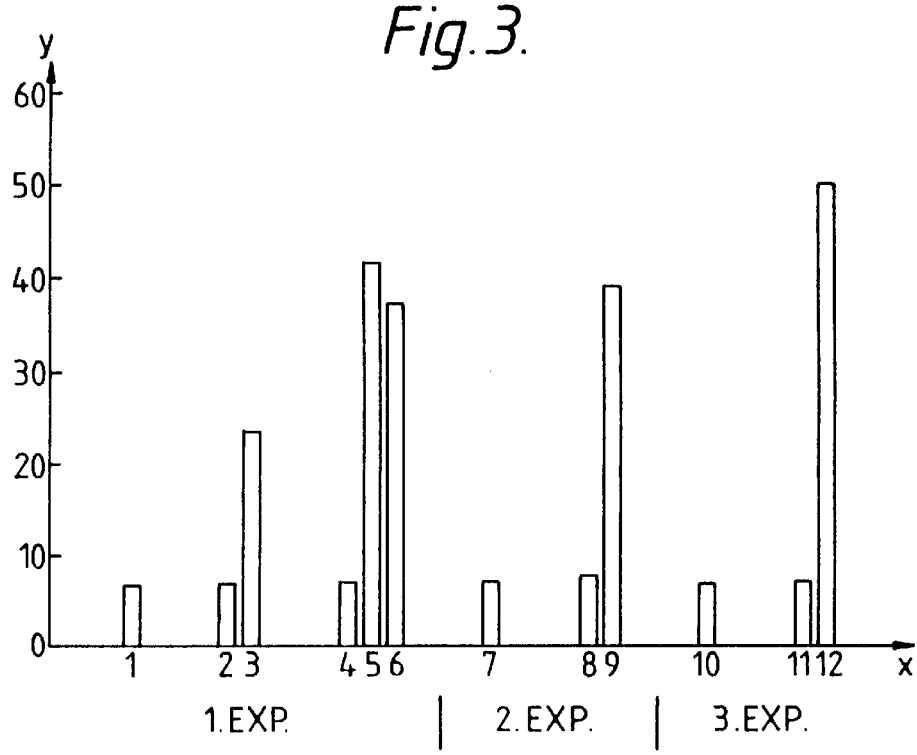

FIG. 3 shows the concentrations in ng/ml of mAb78, unprotected mAb78-mPEG or protected mAb78-mPEG conjugates at which 1 ng/ml huTNFα exerts 50% cytotoxic activity on LM cells (y-axis). (1) mock-derivatized mAb78; (3) unprotected mAb78 derivatized upon addition of a 15-fold molar excess of mPEG (calculated on the mAb78 concentration); (2) protected mAb78 derivatized upon addition of a 15-fold molar excess of mPEG (calculated on the concentration of mAb78+mAb2); (5) unprotected mAb78+mPEG 100×; (6) unprotected mAb78 and mouse IgG derivatized upon addition of a 100-fold molar excess of mPEG (calculated on the mAb78+mouse IgG concentrations); (4) protected mAb78+mPEG 100×; (7) as (1); (8) as (4); (9) as (5); (10) as (1); (12) unprotected mAb78+mPEG 500×; (11) protected mAb78+mPEG 500×.

Figure 4:
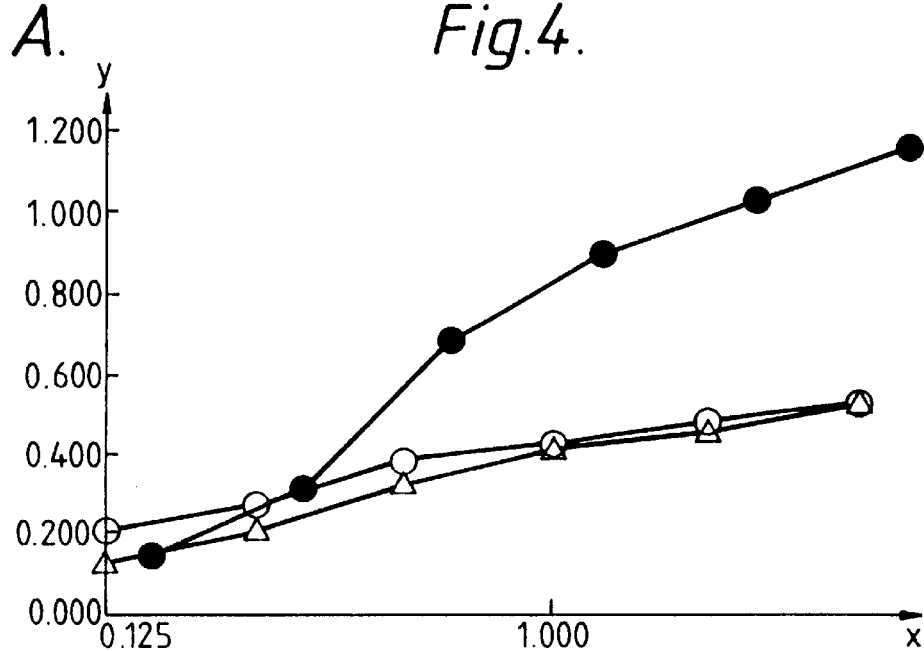
Figure 4:
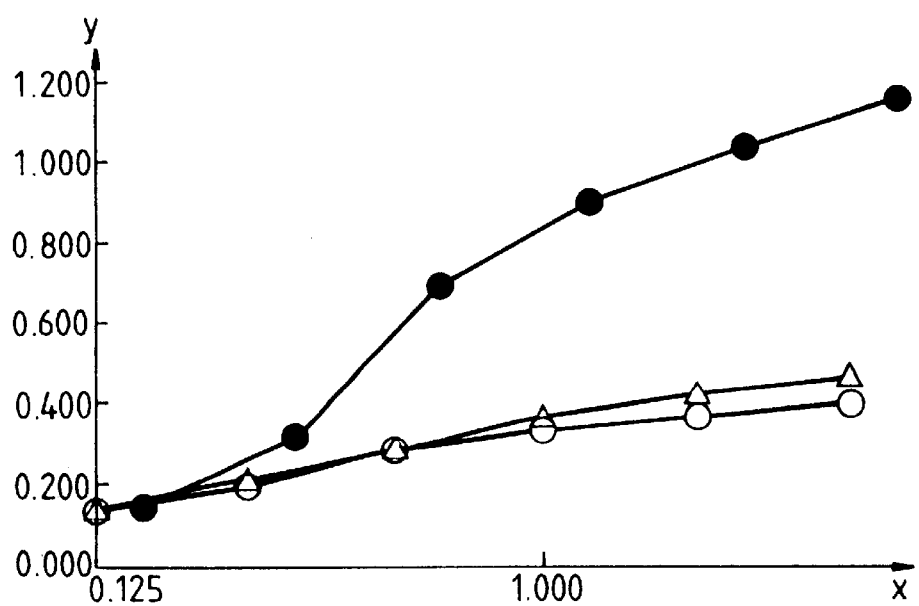

FIG. 4 shows the detection of mAb78, unprotected mAb78-mPEG or protected mAb78-mPEG conjugates in a mouse IgG-specific ELISA. A : (●) mock-derivatized mAb78; (Δ) unprotected mAb78 derivatized upon addition of a 100-fold molar excess of mPEG (unprotected mAb78+mPEG 100×); (O) protected mAb78 derivatized upon addition of a 100-fold molar excess of mPEG. B : (●) mock-derivatized mAb 78; (Δ) unprotected mAb78+mPEG 500×; (O) protected mAb78+mPEG 500×. x-axis: concentration of mAb78 in ng/ml. y-axis: O.D. units.

Figure 5:
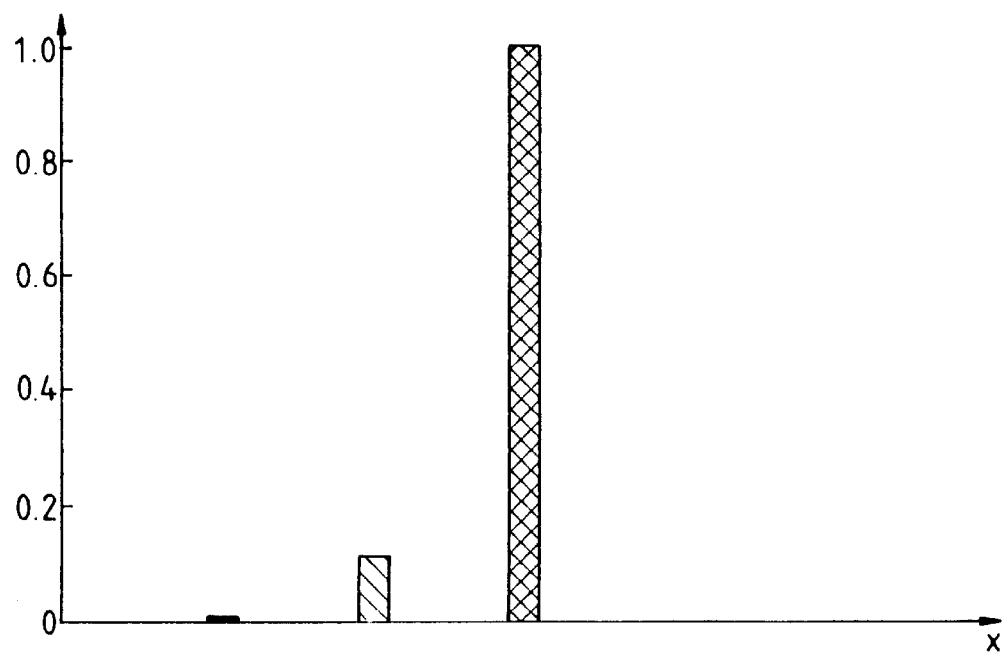

FIG. 5 shows the inhibition of the binding of $^{125}$I-huTNFα to recombinant TNF-R1 receptor by unprotected huTNFα-mPEG or huTNFα-mPEG protected with insolubilized anti-huTNFα mAb78. y-axis: amount of competitor in μg. ■ denotes huTNFα, ▨ denotes huTNFα-PEG30× and ▧ denotes protected huTNFα-PEG30×.

A further object of the present invention is to provide a conjugate between a polymer and an anti-tumor necrosis factor α(antibody preferably a monoclonal antibody against human TNFα.

The polymer is generally an inert, synthetic, polymeric carrier. The polymer is usually water soluble. Preferred examples of polymers according to the invention are poly(ethylene glycol) (PEG), poly(vinyl pyrrolidone), poly(vinyl alcohol), poly(amino acids), divinylether maleic anhydride, ethylene-maleic anhydride, N-(2-hydroxypropyl)-methacrylamide or dextran.

The monoclonal antibody against TNF may be either a human or non-human antibody, typically mAb78 as disclosed in EP-A-0492488.

The conjugates between a polymer and a monoclonal antibody against TNF according to the invention can be administered to mammals, comprising humans, according to the diseases and administration routes well known to the people skilled in the art.

The conjugates between a polymer and anti-tumor necrosis factor-α antibody of the present invention can be employed in mammals, including humans, for prophylactic and/or therapeutic use in any disease state in which TNFα and/or TNFβ are known to exert a pathogenic effect. Typically such disease states are cachexia, septic shock, graft-versus-host disease, AIDS, cerebral malaria, rheumatoid arthritis, chronic and acute inflammatory diseases, myocardial ischaemia and others in which it is already known or will be known in the future that TNFα and/or TNFβ play a detrimental role. For instance doses ranging from about 0.5 to about 20 mg/kg of body weight can be used for parenteral administration in adult humans, e.g. in treating septic shock for adduct PEG-mAb78. Single or multiple administrations of the compositions can be carried out with dose levels and pattern being selected by the treating physician. In any event, the pharmaceutical formulations should provide an antibody quantity sufficient to effectively treat or prophylactically treat the patient.

Object of the invention is also a pharmaceutical composition comprising a suitable carrier and/or diluent and, as an active principle, a conjugate between a polymer and an antibody against TNFα, preferably a monoclonal antibody against human TNFα.

The conjugates of this invention can be formulated according to well known methods by including appropriate amounts of the conjugates with a pharmaceutically acceptable carrier and/or diluent.

The following are examples of possible formulations:

1. CONJUGATE PEG-mAb78 LYOPHILIZED FORMULATION CONTAINING: (composition of the pre-lyophilization solution)

| | |
|---|---|
| Active Drug | from about 0.05% to about 0.5% w/v |
| Bulking Agent* | from about 2.50% to about 5.0% w/v |
| Surface-Active Agent** | from about 0.0025% to about 0.025% w/v |
| pH-Adjusting Agent*** | q.s. to pH 6.5–7. |

2. CONJUGATE PEG-mAb78 "READY-TO-USE" FORMULATION CONTAINING:

| | |
|---|---|
| Active Drug | from about 0.05% to about 0.5% w/v |
| Surface-Active Agent** | from about 0.0025% to about 0.025% w/v |
| pH-Adjusting Agent*** | q.s. to pH 6.5–7 |
| W.F.I. | q.s. |

In order to make an isotonic aqueous solution, an external agent (e.g. sodium chloride, sorbitol or dextrose) may be added at its isotonic level.

* e.g.: Lactose or Mannitol;
** e.g.: Polysorbates or Poloxamer;
*** e.g.: NaOH 0.01 N or HCl 0.01N
W.F.I means water for injections.

EXAMPLE 1
Preparation of antiidiotypic mAb2

The antiidiotypic monoclinal antibody (mAb2) was generated as previously described (M.Nonestier, Cancer Research 49 : 123–126, 1989). BALB/C mice were immunized two times by i.p. injection of 100 μg/mouse of purified BSA-mAb78 in Complete Freund's Adjuvant. Animals were boosted i.p. three times, every two weeks, with 100 μg/mouse of BSA-mAb78 in PBS.

The animals were sacrified three days after the last immunization and their splenocytes fused with non-secreting murine myeloma NSO according to standard techniques (Galfre, C. Methods of Enzymology 73 : 3–46, 1981).

Culture supernatants from grown hybridomas were then screened by ELISA for the presence of antiidiotypic antibodies.

Briefly, goat-anti-mouse Ig was diluted at 10 μg/ml in phosphate buffer pH 7.2 and added (100 μl/well) to a polyvinylchloride flat bottom-microtitration plate (Falcon 3912).

After overnight incubation at 4° C. the plate was saturated with 100 μl/well of BSA (1% in PBS) for 3 hours at room temperature.

Culture supernatants, were added (50 μl/well) and incubated 1 hour at 37° C.

After washing, the biotinylated mAb78 (0.25 μg/ml in PBS –0.05% Tween –1% BSA) was added and incubated for 1 hour at 37° C. After washing, avidin-peroxidase (Vector Laboratories, Burlingame, Calif.) was added at 0.25 μg/ml in PBS-Tween-BSA for 1 hour at 37° C. After extensive washing, 100 μl of peroxidase substrate (OPD2, Chemicon, SCI. Rome, Italy, 1 Tablet in 5 ml of citrate buffer, OPD4, Cbemicon), was added to each well.

The reaction was stopped after 2 minutes with 100 μl/well of 4M $H_2SO_4$ and optical density was read at 492 nm.

One of the positive hybridomas, selected for the production of antiidiotypic monoclonal antibodies able to interfere with the binding of mAb78 to huTNFα was cloned twice by limiting dilution.

The clone 65 producing the antiidiotypic monoclonal antibody (mAb2) was expanded, the mAb2 produced was purified from the supernatant and used to protect the binding side of mAb78 to huTNFα in the experiments of Example 2 which follows.

EXAMPLE 2

1. METHODS

1. Derivatization of a mAb1 with MPEG according to the prior art.

For this purpose 400 μg of mAb78 (EP-A-0492488; mAb1) were incubated for 30 minutes in 1 ml PBS (phosphate buffered saline) pH 7.2 in the absence or presence of different molar excesses of mPEG (monomethoxy-polyethylene glycol succinimidyl succinate, Polymer Labs., Church Stretton, UK). mAb78 is a mAb against hu TNFα. In one instance a dose of mouse IgG equivalent to that of antiidiotypic NAb2 employed in the protected derivatization (800 μg, see below) was added and the molar excess of mPEG was calculated on the concentration of mAb78+ mouse IgG. At the end of the incubation, bovine serum albumin (BSA, Armour, Kankakee, Ill.) was added to a final concentration of 0.5% to quench free, unreacted mPEG.

2. Covalent coupling of a mAb2 to solid-phase.

For this purpose 5 mg of mAb2 were coupled to $CNB_r$-activated Sepharose (Pharmacia LKB, Uppsala, Sweden) following the manufacturer's instructions.

3. Protected derivatization of mAb78 with mPEG.

Sepharose-bound mAb2 (800 μg) was incubated with 400 μg mAb78 in 1 ml PBS pH 7.2 for 4 h under constant agitation at room temperature. Then, after centrifugation, the bead-pellet was resuspended for 30 mintues under the same conditions in 1 ml PBS pH 7.2 without or with different molar excesses of mPEG (calculated on the mAb78+mAb2 concentration). Sepharose-bound mAb78/mAb2 complexes were than centrifuged 4 times, then resuspended in glycine-HCl, pH 4 buffer, recentrifuged and resuspended for 5 min in glycine-HCl, pH 2.8 buffer to elute mAb78. Upon a final centrifugation supernatants were collected, adjusted to neutral pH and eluted mAb78 was quantified by means of a commercially available kit (Bio-Rad Micro-Assay, Segrate, Italy) following the manufacturer's intructions. Thereafter BSA was added to a final concentration of 0.5% to quench free, unreacted mPEG.

4. Determination of the neutralizing activity of mAb78 or mAb78 -mPEG conjugates.

On day 0 logarithmically growing mouse LM cells (Rubin, B. Y. et al, *J. Exp. Med.,* 162 : 1099 (1985)) were trypsinized, centrifuged and resuspended at a final concentration of 3×10⁵ cells/ml of Eagle's minimum essential medium supplemented with 5% FCS and 2mM glutamine (complete MEM).

100 μl of this suspension were added to the wells of flat bottom microtiter plates (Falcon 3072). Then a dilution of huTNFα (Esquire Chemie, Zuerich, Switzerland) was set up in complete MEM to have a final concentration, after addition to wells, of 1 ng/ml.

mAb78 or mAb78-mPEG conjugates were diluted in complete MEM and added to wells to have final concentrations from 200 ng/ml to 0.35 ng/ml.

50 μl of diluted huTNFα were then incubated with 50 μl of each mAb78 or mAb78-mPEG conjugate dilution or with 50 μl complete MEM for 2 hours at 37° C. During this incubation period a solution containing actinomycin D (Fluka, Buchs, Switzerland) was set up in complete MEM. The final concentration of actinomycin D after addition to the wells was 2 μg/ml. At the end of the incubation period each mAb78-huTNFα or mAb78-mPEG conjugate-huTNFα mixture and 50 μl of actinomycin D were added to the wells of microtiter plates. To some wells 100 μl of huTNFα alone were added. To some controls wells only actinomycin D-solution and complete MEM were added. Thereafter the plates were incubated for 24 hours at 37° C.

After the incubation a fresh solution of MTT (CALBIOCHEM 589511 - La Jolla - Calif.) 5 mg/ml in PBS was prepared and 40 μl were transferred into each well. The plates were incubated at 37° C., 5% $CO_2$ for 4 hours. At the end of the incubation the medium was aspirated. DMSO (CARLO ERBA-ITALY) was then added (200 μl/well) and vigorously pipetted 2–3 times. The plates were then read in the spectrophotometer at 570 nm wavelength.

The data were expressed in optical density (OD) UNITS. The OD values were expressed as percent values of those from the control wells (Actinomycin D alone).

These percent values were processed by means of the ELISA-Soft PC program (PERKIN-ELMER-NORWALK, Conn. USA) and the mAb78 concentration giving 50% cytotoxicity in the presence of 1 ng/ml huTNFα was thereby determined.

5. ELISA for the determination of mAb78 or mAb78-mPEG conjugates.

Flat-bottom microtiter plates were coated at 100 μl/well with goat-anti mouse Ig (Biosys, Compiegne, France, 1 μg/well) diluted in 40 mM phospate buffer pH 7.4). After overnight incubation at 4° C., unabsorbed antibody was discarded and PBS pH 7.2, supplemented with 1% BSA, was added to each well to saturate unoccupied plastic sites. The plates were further incubated for 3 hours at room temperature and thereafter washed 3 times with washing buffer (WB), that is PBS pH 7.2 supplemented with 0.1% Tween 20 (Merck, Schuchardt, Hohenbrunn, FRG) and 0.01% merthiolate (BDH, Pool, GB). During this incubation period, serial two-fold dilutions of mAb78 or mPEG-mAb78 conjugates were set up. All dilutions were in PBS pH 7.2, 1% BSA. 50 μl of each dilution were added to the wells, the plates incubated for 60' at 37° C. and then washed as above. Then, 100 μl of peroxidase-conjugated goat anti-mouse IgG (Biosys, Compiegne, France) diluted 1:2000 in WB were added to each well, the plates incubated for 45 minutes at 37° C. and washed as above. Then, 100 μl of peroxidase substrate (OPD2, Chemicon, SCI, Rome, Italy, 1 tablet dissolved in 5 ml citrate buffer, OPD4, Chemicon) were added to each well. The reaction was allowed to proceed for 2' at room temperature, after which color development was stopped by the addition of 100 μl/well of 4 M $H_2SO_4$. The extent of color development was read on a plate ELISA reader at 492 um.

2. RESULTS

Derivatization of a mAb1 with mPEG according to the prior art

In order to evaluate the effect of non-specific polymer-derivatization of a molecule (the conjugate being prepared according to the prior art) on its biological activity, we chose as a model system a mAb1 against huTNFα. This mAb1 (mAb78; EP-A-0492488) neutralizes the cytotoxic activity of huTNFα on mouse LM cells. Thus, 1 ng/ml huTNFα kills 85–90% of LK cells in such a cytotoxicity assay. Upon incubation of 1 ng/ml huTNFα with increasing concentrations of mAb78, a dose-dependent inhibition of the cytotoxic activity is observed (FIG. 1). In this assay, 1 ng/ml huTNFα exerted 50% cytotoxic activity in the presence of 6.7 ng/ml mAb78.

We then synthesised a conjugate of mAb78 with MPEG (prepared according to the prior art) using different molar ratios of mPEG/mAb78. Increasing concentrations of each mAb78-mPEG conjugate were incubated with 1 ng/ml huTNFα and the concentration of each conjugate at which 50% cytotoxicity was observed was determined. As can be seen from FIG. 2, there was a correlation between the increase of the mAb78-mPEG concentration required to give 50% cytotoxicity and increasing molar ratios of mPEG/mAb78 conjugates. At the highest ratio employed (500:1) 50% cytotoxicity was observed at a mAb78-mPEG concentration of 49 ng/ml. These results show that polymer-derivatization of mAb78 according to the prior art causes, at increasing molar ratios of mPEG/mAb78 employed during the conjugation step, an increasing loss of biological activity. This is reflected in the increasing mAb78-mPEG concentrations required to reduce the cytotoxic activity of 1 ng/ml huTNFα from 85–90% to 50%.

Protected derivatization of a mAb1 with mPEG according to the present invention

In order to perform the conjugation step under conditions whereby the antigen (huTNFα)-binding regions of mAb78 are protected from polymer derivatization according to the present invention, we took advantage of an antiidiotypic mAb (mAb2) that interferes with the binding of mAb78 to huTNFα, and consequently with the neutralization of huTNFα by mAb78. This property assures that mAb2 shields, during the conjugation process, the mAb78-domains involved in huTNFα-binding, thereby preserving the antigen (huTNFα)-binding and neutralizing activity of mAb78.

We therefore performed derivatization of mAb78 in the presence of protection afforded by mAb2 at mPEG/mAb78+mAb2 ratios of 15:1, 100:1, 500:1. Derivatized mAb78 was recovered upon elution with 0.1 M glycine-HCl pH-2.8. The results of the 3 experiments that have been performed are shown in Table 1 and FIG. 3. In each experiment we included as a control mock-derivatized mAb78, i.e. mAb78 that was submitted to the same procedure as the aforementioned samples but without adding IPEG. Still another control included in each experiment was mAb78 derivatized according to the prior art, i.e. without protection afforded by mAb2. A control included in experiment 2 was mAb78 derivatized without protection in the presence of mouse IgG at a concentration equivalent to that of mAb2 used for the protected derivatization.

The results show that when mAb78 was derivatized without protection afforded by mAb2, either in the presence or absence of mouse IgG, the expected decrease in neutralizing activity was observed. On the other hand, derivatization performed according to the present invention allowed the recovery of mAb78-mPEG conjugates with fully preserved biological activity. These results show that polymer-derivatization of bioactive molecules according to the present invention, i.e. having the active domains protected through interaction with a specific binder, during the conjugation step, allows indeed a full recovery of the desired biological activity(ies).

Recognition of protected and unprotected mAb78-mPEG conjugates by Anti-mouse IgG antibodies.

It is well known from the prior art that polymer-derivatized proteins, that are heterologous with respect to the species to be treated, are recognized much less efficiently by antibodies produced upon administration of the underivatized protein (see, generally, Fuertges, F. and Abuchowski, A., *Journal of Controlled Release,* 11 : 139–148, 1990).

We therefore compared the reactivity of mAb78-mPEG conjugates, that had been generated without or with protection afforded by mAb2, with anti-mouse IgG antibodies in ELISA. Such antibodies react with antigenic determinants common to all mouse antibodies of IgG isotype and, therefore, also with mAb78 which is an IgGl,k antibody. As can be seen from FIG. 4, the reactivity of the protected as well as that of the unprotected mAb78-mPEG conjugates was similarly decreased compared to unconjugated mAb78.

EXAMPLE 3

Methods

1. Derivatization of huTNFα with mPEG according to the prior art

For this purpose 200 μg of recombinant human TNF-α (WOC Ltd. Vaduz, Luxemburg; specific activity: $3.2\times10^7$ units/mg; purity: >97%) were incubated for 3 h in 0.2 ml, 25 mM sodium borate buffer, pH 8.0, in the absence or presence of different molar excesses of mPEG (Methoxypolyethylene glycol-Cyanuric chloride; Sigma M3277, Milano, Italy). At the end of the incubation, MPEG excess removed by gel filtration on a Sephacryl S200 column (Pharmacia, Uppsala, Sweden) equilibrated with PBS, pH 7.2. Protein concentration was quantified by means of commercially available kit (Bio-Rad Micro-assay, Segrate, Italy) following the manufacturer's instructions.

2. Covalent coupling of mAb 78 to solid-phase.

For this purpose, 2 mg of mAb 78 were coupled to 1 ml AFFI-gel 10 (Bio-Rad, Segrate, Italy) following the manufacturer's instructions.

3. Protected derivatization of huTNFα with mPEG. Sepharose-bound mAb 78 (400 μg) was incubated with 100 μg huTNFα in 1 ml PBS pH 7.2 for 4 h under constant rotation at room temperature. Then, after centrifugation and washings, the bead-pellet was resuspended for 3 h under the same conditions in 25 mM sodium borate buffer, pH 8.0, and different molar excesses of mPEG were added (calculated on the mAb 78+huTNFα concentration). The Sepharose bound huTNF α/mAb78 complex was washed 4 times, then resuspended in universal buffer (6.7 mM citric acid, 6.7 mM orthophosphoric acid, 11.4 mM orthoboric acid), pH 3.0 to elute huTNFα. After a final centrifugation, supernatants were collected, adjusted to neutral pH and eluted huTNFα was quantified by means of commercially available kit (Bio-Rad Micro-assay, Segrate, Italy) following the manufacturer's instructions. mPEG incorporation was assessed by means of HPLC analysis, on a Superose 6 HR 10/30 column (Pharmacia, Uppsala, Sweden) equilibrated with 0.1 M sodium phosphate buffer, pH 7.0, as molecular weight increase in comparison with the native protein. The column was calibrated using commercially available molecular weight standards (Bio-Rad cat.151–1901; Milan, Italy).

4. Cloning and expression of the extracellular domain of 55kDa human TNF receptor.

Human recombinant TNFα receptor, extracellular portion of the p55 receptor, linked to a poly-histidine codon, molecular weight 19 Kd; was cloned, produced and purified to homogenity (over 95% as determined by SDS-PAGE) by Farmitalia Carlo Erba, Milan Italy according to the procedure described by Fountoulakis M. et al, 1990, J.B.C. 265, 13268–13275. The cDNA for the 55kDa human TNF receptor, was isolated by screening a λgt11 library (Clontech) using as probe two synthetic oligonucleotides designed according to the published nucleotide sequence of the 55kDa receptor (Gray et al. 1990 PNAS USA 87, 7380–7837.

The CDNA coding the extracellular domain of 55kDa TNFR was cloned in a plasmid of the pQE series type IV (DIAGEN GmbH -Hilden- Germany) fused in frame to a polyHis tail.

The insertion of the cDNA was carried out following amplification by Polymerase Chain Reaction (PCR); PCR primers were selected to introduce restriction sites compatible with the sites present in the pQE9 polylinker; in addition a translation stop codon was engineered behind the nucleotides corresponding to the last aminoacid of the extracellular domain. The plasmid, called pFC228, was transformed in a K12 derived E.coli strains: M15(pREP4). The new strain was called FICE 284.

5. Radioimmunoassay for the determination of the binding of TNFα-mPEG conjugates to insolubilized recombinant TNF-R1 receptor Round bottom microtiter plates were coated with 0.1 ml of recombinant external domain of the TNF-R1 receptor as obtained from FICE 284 (120 ng/well in 0.1 M carbonate buffer, pH 9.6). After an overnight incubation at 4° C., plates were washed three times with WB, overcoated with 1% BSA for 1 h at room temperature and washed as before. Plates were then added with 50 μl of $^{125}$I-huTNFα (specific activity: 40.3 μCi/ug; NEN Dreieich, W. Germany) plus 50 μl of serial two-fold dilutions of huTNFα, unprotected huTNFα-mPEG or huTNFα-mPEG protected by insolubilized mAb 78. Following a 2 h incubation, plates were washed three time with WB and the radioactivity present in each well was measured in a gamma counter.

Results

Derivatization of human TNF-α with mPEG according to the prior art

In order to evaluate the effect of non-specific polymer-derivatization on huTNFα, we prepared a series of conjugates of huTNFα with 10, 20 and 30 molar excesses of mPEG and tested them in a cytotoxicity assay and in a binding assay to huTNFα receptor. The cytotoxic activity of the native and derivatized huTNFα was determined using mouse LM cells. Derivatized huTNFα displayed a substantial dose-dependent decrease of cytotoxicity with respect to the native protein (Table 2). When tested in a binding assay, all conjugates showed a substantial loss of their ability to displace the binding of $^{125}$I-huTNFα from insolubilized human TNFα receptor (FIG. 5). Loss of binding of mPEG-huTNFα to the receptor was evident even when the conjugates where tested at concentrations 100 fold higher with respect to the amount of native molecule able to displace 50% of the radioactivity.

Protected derivatization of huTNFα with mPEG according to the present invention.

In order to evaluate the effect of protection by a monoclonal antibody on the binding site of huTNFα to its specific receptor, we prepared a series of conjugates between huTNFα and mPEG at 10 and 30 fold molar excesses (calculated on the mAb 78+huTNFα concentration) after binding huTNFα to insolubilized mAb 78. The latter monoclonal antibody, being able to neutralize the cytotoxic activity of the huTNFα, probably recognizes an epitope involved in the recognition of the cytokine by its receptor. After derivatization, products were analyzed by HPLC. Both the protected and unprotected conjugates displayed a molecular weight substantially higher (128 Kd) than the native TNF-α (34 Kd). The cytotoxic activity of the protected derivatized huTNFα was determined using mouse LM cells. The protected conjugates displayed a better retention of biological activity in comparison with the analogous unprotected conjugates (Table 2). Moreover, the protected conjugates were able to displace the binding of $^{125}$I-huTNFα to insolubilized recombinant human TNFA receptor at concentration significantly lower than the analogous unprotected conjugates (FIG. 5).

It can be therefore concluded that polymer-derivatization of bioactive molecules according to the present invention, whereby the domain(s) mediating the desired biological activity(ies) are protected through interaction with a specific binder, results in a greatly decreased reactivity with antibodies raised against the underivatized molecule, a decrease similar to that observed upon derivatization performed according to the prior art. In the latter case, however, this is obtained at the expense of a significant loss of the desired biological activity, whereas for conjugates obtained according to the present invention, the biological activity is preserved.

TABLE 1

Concentrations of mAb78, unprotected nAb78-mPEG conjugates or protected mAb78-mPEG conjugates at which 1 ng/ml huTNFα exerts 50% cytotoxic activity on LM cells.

|  |  | Concentration (ng/ml) |
|---|---|---|
| 1. Experiment | mAb78[a] | 6.7 |
|  | Unprotected mAb78 + mPEG 15x[b] | 23.6 |
|  | Unprotected mAb78 + mPEG 100x | 41.61 |
|  | Unprotected mAb78 + mouse IgG + mPEG 100x[c] | 37.32 |
|  | Protected mAb78 + mPEG 15x[d] | 7.0 |
|  | Protected mAb78 + mPEG 100x | 7.16 |
| 2. Experiment | mAb78 | 6.93 |
|  | Unprotected mAb78 + mPEG 100x | 39.06 |
|  | Protected mAb78 + mPEG 100x | 7.06 |
| 3. Experiment | mAb78 | 7.2 |
|  | Unprotected mAb78 + mPEG 500x | 49.0 |
|  | Protected mAb78 + mPEG 500x | 7.8 |

[a]Mock-derivatized mAb78
[b]Unprotected mAb78 derivatized upon addition of a 15-fold molar excess of mPEG (calculated on the mAb78 concentration)
[c]Unprotected mAb78 and mouse IgG derivatized upon addition of a 100-fold molar excess of mPEG (calculated on the mAb78 + mouse IgG concentration)
[d]Protected mAb78 derivatized upon addition of a 15-fold molar excess of mPEG (calculated on the concentration of mAb78 and that of the specific binder mAb2).

TABLE 2

Doses of protected and unprotected TNFα-mPEG giving 50% of cytotoxicity on LM cells.

| mPEG (cyanuric-chloride) | huTNFα-mPEG | Protected huTNFα-mPEG |
|---|---|---|
| 0 | 0.03 ng/ml | 0.03 ng/ml |
| 10x | 1.09 ng/ml | 0.14 ng/ml |

TABLE 2-continued

Doses of protected and unprotected TNFα-mPEG giving 50% of cytotoxicity on LM cells.

| mPEG (cyanuric-chloride) | huTNFα-mPEG | Protected huTNFα-mPEG |
|---|---|---|
| 20x | 3.90 ng/ml | — |
| 30x | 5.40 ng/ml | 0.25 ng/ml |

What is claimed is:

1. A process for the preparation of a conjugate between a poly (ethylene glycol) and a monoclonal antibody having an antigen-binding domain, the process comprising specifically binding the domain to an antiidiotypic antibody, to shield the domain from the poly (ethylene glycol) in the following conjugating step;

thereafter, conjugating the poly (ethylene glycol) to the monoclonal antibody, wherein conjugation of the poly (ethylene glycol) to the domain is avoided; and thereafter, releasing the antiidiotypic antibody from the domain without releasing the poly (ethylene glycol) from the monoclonal antibody.

2. A process for the preparation of a conjugate between a poly (ethylene glycol) and a protein or glycoprotein having a domain, the process comprising specifically binding the domain to a specific binder wherein said binder is a protein, to shield the domain from the poly (ethylene glycol) in the following conjugating step;

thereafter, conjugating the poly (ethylene glycol) to the protein or glycoprotein, wherein conjugation of the poly (ethylene glycol) to the domain is avoided; and thereafter, releasing the specific binder from the domain without releasing the poly (ethylene glycol) from the protein or glycoprotein, wherein the protein or glycoprotein is other than a proteolytic enzyme selected from the group consisting of trypsin, urokinase, tissue plasminogen activator, plasmin, chymotrypsin, elastase and kallikrein.

3. The process of claim 2, wherein the protein or glycoprotein is a monoclonal antibody, or a Fab' or F(ab)$_2$ fragment thereof.

4. The process of claim 2, wherein the specific binder is an antibody or antiidiotypic antibody.

5. The process of claim 3, wherein the specific binder is an antigen which is known to specifically bind to the monoclonal antibody or fragment thereof.

6. The process of claim 2, wherein the protein or glycoprotein is a non-human monoclonal antibody against human tumor necrosis factor alpha antigen and the domain is the antigen-binding region.

7. The process of claim 6, wherein the specific binder is a non-human antiidiotypic antibody which specifically binds to the domain.

8. The process of claim 2, wherein said process is conducted in solution and said releasing step comprises raising or lowering the pH of the solution to effect dissolution of the specific binder from the domain.

* * * * *